United States Patent [19]

Balazs et al.

[11] Patent Number: 4,713,448

[45] Date of Patent: Dec. 15, 1987

[54] CHEMICALLY MODIFIED HYALURONIC ACID PREPARATION AND METHOD OF RECOVERY THEREOF FROM ANIMAL TISSUES

[75] Inventors: Endre A. Balazs, Ft. Lee; Adolf Leshchiner; Adelya Leshchiner, both of Fairview, all of N.J.; Philip Band, Brooklyn, N.Y.

[73] Assignee: Biomatrix, Inc., Ridgefield, N.J.

[21] Appl. No.: 710,929

[22] Filed: Mar. 12, 1985

[51] Int. Cl.$^4$ .................. C08B 37/08; C08F 8/00; C12P 19/04; C12R 1/46
[52] U.S. Cl. ..................... 536/55.1; 435/267
[58] Field of Search ................ 435/267; 536/55.1

[56] References Cited

U.S. PATENT DOCUMENTS

| | | | |
|---|---|---|---|
| 3,396,081 | 8/1968 | Billek | 536/55.1 |
| 4,141,973 | 2/1979 | Balazs | 514/769 |
| 4,272,522 | 6/1981 | Balazs | 424/94 |
| 4,303,676 | 12/1981 | Balazs | 514/777 |
| 4,487,865 | 12/1984 | Balazs et al. | 525/54.2 |
| 4,500,676 | 2/1985 | Balazs et al. | 524/29 |
| 4,517,295 | 5/1985 | Bracke et al. | 536/55.1 |
| 4,582,865 | 4/1986 | Balazs et al. | 524/27 |
| 4,605,691 | 8/1986 | Balazs et al. | 524/27 |
| 4,629,623 | 12/1986 | Balazs et al. | 424/63 |

Primary Examiner—Ronald W. Griffin
Attorney, Agent, or Firm—Sheldon Palmer

[57] ABSTRACT

Disclosed is hylan, a chemically modified hyaluronic acid preparation characterized by the presence of small amounts (0.005–0.05% by weight) of aldehyde cross-linking groups covalently bonded to the hyaluronic acid molecular chains. Also disclosed is a method of obtaining hylan comprising treating hyaluronic acid in situ in animal tissues containing same with a treatment mixture including a reagent (typically an aldehyde) which is reactive towards hyaluronic acid and the proteins contained in the animal tissue.

27 Claims, 8 Drawing Figures

CHEMICALLY MODIFIED HYALURONIC ACID PREPARATION AND METHOD OF RECOVERY THEREOF FROM ANIMAL TISSUES

BACKGROUND OF THE INVENTION

1. Field of the Invention

The invention relates to a chemically modified hyaluronic acid preparation characterized by novel chemical, physicochemical and rheological properties, and a novel method for obtaining such preparation.

2. The Prior Art

Hyaluronic acid (hereinafter referred to as HA) is a naturally occuring high molecular weight glycosaminoglycan having a repeating disaccharide unit of D-glucuronic acid and N-acetylglucosamino-2-acetamido-2-desoxy-D-glucose joined by $\beta 1 \rightarrow 3$ glucosidic bond. The disaccharides are joined to form an unbranched, uncrosslinked polysaccharide chain by $\beta 1 \rightarrow 4$ glucosidic bonds.

HA is found in animal tissues such as umbilical cord, vitreous, synovial fluid, rooster combs, skin, etc. The molecular weight of purified HA has been reported in the literature to be within the range of 50,000 to 8,000,000 depending on the source, method of isolation and method of determination of molecular weight (Balazs, E. A., Fed. Proceed. 17, 1086–1093 (1958)).

Several method have been suggested for recovery and purification of HA from animal tissues and bacterial cultures. Among these are enzymatic digestion of proteins (E. D. T. Atkins, C. F. Phelps and J. K. Sheehan, Biochem. J. 128, 1255–1263, (1972); R. Varma, R. S. Varma, W. S. Alten and A. H. Wardi, Carbohydr. Res. 32, 386–395, (1974); treatment with ion exchange resins (T. C. Laurent, J. Biol. Chem. 216, 263–271, (1955); E. R. Berman, Biochim. Biophys. Acta 58, 120–122 (1962)); precipitation with cationic surfactants (T. C. Laurent, M. Ryan, and A. Pietruszkiewicz, Biochem. Biophys. Acta 42, 476–485 (1960)); treatment with trichloroacetic acid (H. Hofmans, O. Schmut, H. Sterk, and H. Koop, Naturforsch. 34c, 508–511 (1979); D. Schmut, and H. Hofmans, Biochim Biophys. Acta 673, 192–196 (1981)); preparative density gradient sedimentation (P. Silpanata, J. R. Dunstone, A. G. Ogston, Biochem. J. 109, 43–50 (1968)); and electrodeposition (S. Roseman, D. R. Watson, J. F. Duff, and W. D. Robinson, Annals Rheumatic Diseases, 15, 67–68 (1955)). One can also use a method which contains several different treatments, e.g., enzymatic digestion and precipitation with cetylpyridinium chloride (J. E. Scott, Biochem. J., 62, 31 (1956)).

The principal problem encountered in recovering HA from any biological source involves separating the polymer (HA) from proteins and other biological polymers which are extracted from the tissue along with the HA. Depending upon the raw material, the amount of undesirable polymers can be very large, exceeding by many times the amount of HA. The methods of HA recovery cited above are all used for the preparation of HA in laboratories but can hardly be used for large scale production of HA because of various drawbacks inherent in each of those methods.

The most advanced method for HA recovery and purification on an industrial scale is described in U.S. Pat. No. 4,141,973 (E. A. Balazs). According to this method, an ultrapure HA with a protein content of less than 0.5% by weight and a molecular weight more than 1,200,000 is obtained by water extraction from rooster combs or human umbilical cord. Proteins and other substances are removed with several chloroform extractions at varying pH values. In a chloroform extraction of the water extract an interface layer is formed in which denatured proteins and other substances are collected. Some substances, e.g., fats, are solubilized, probably in the chloroform phase. The process can also include a treatment with a proteolytic enzyme, e.g. pronase. By combining several quite elaborate treatments a process has been developed which allows one to obtain a pyrogen-free, non-inflammatory fraction of HA. This product is presently being marketed as a 1% solution under the trademark Healon ® and is used in viscosurgery where it protects tissues against mechanical damage, provides space and permits manipulation of tissues during surgery (E. A. Balazs, Healon, J. Wiley and Son, NY, 1983, pp 5–28).

SUMMARY OF THE INVENTION

Figure 1:
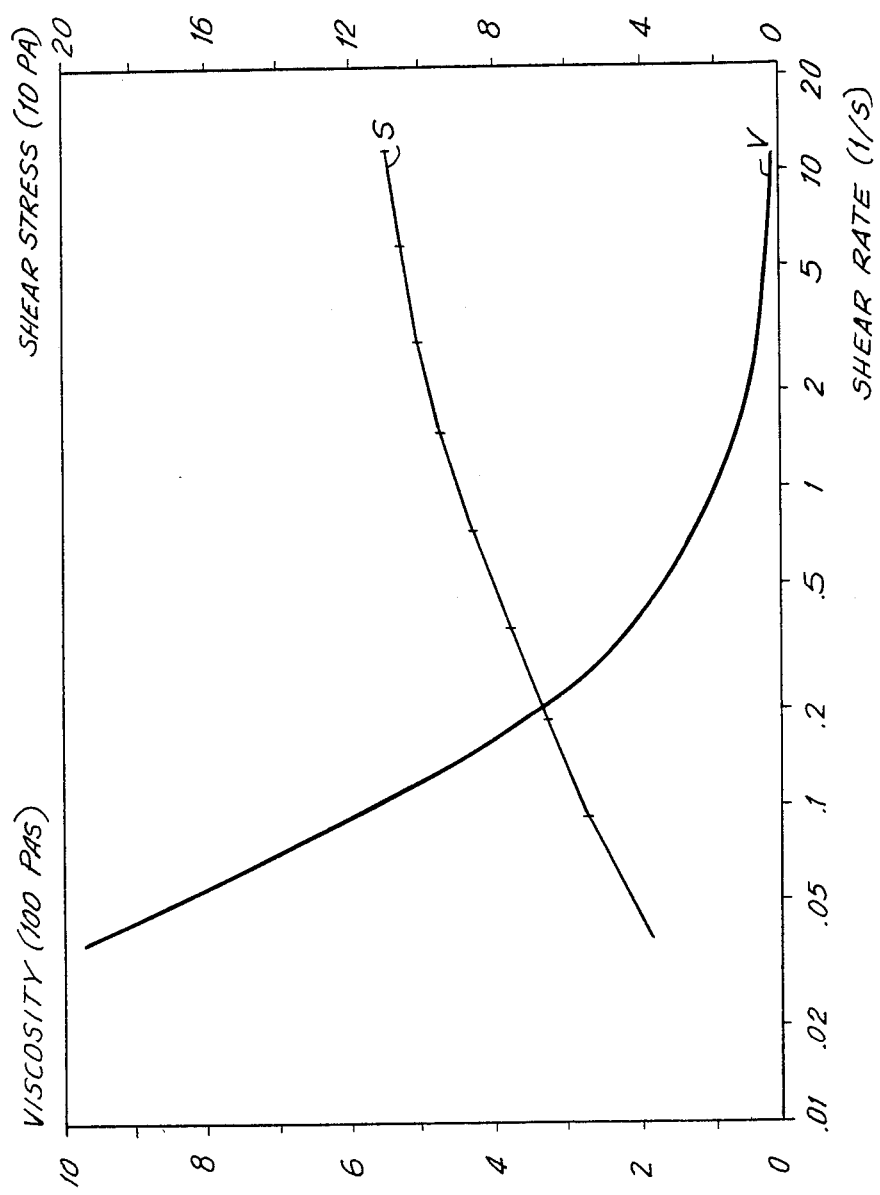
FIG. 1 is a graph showing viscosity vs. shear rate dependence for a 1% (wt.) solution of HY in aqueous 0.15 M NaCl (V=viscosity; S=shear stress)

In one aspect, the present invention provides a novel method for the in situ chemical modification of HA in animal tissues prior to its extraction therefrom.

In another aspect, the invention provides a novel method for recovery and purification of the chemically modified HA from animal tissues.

In still another aspect, the invention provides a novel ultra-pure, pyrogen-free, non-inflammatory chemically modified HA containing about 0.005 to 0.05% by weight of aldehyde cross-linking groups covalently bonded to the hyaluronic acid polymer chains.

DETAILED DESCRIPTION OF THE INVENTION

The present invention is based on our discovery that HA can be chemically modified in situ before it is extracted from animal tissues by treatment of the tissue with a substance that reacts with proteins and HA in aqueous media. Among these substances are formaldehyde, glutaraldehyde, glyoxal, etc. It has been found that this in situ chemical modification produces substantial changes in the primary structure of the HA macromolecule, in molecular size, inter- and intramolecular interactions and in the resulting rheological properties of solutions made from the modified product. It is, therefore, warranted to give this chemically modified HA a new name. We have chosen to call this material Hylan (hereinafter referred to as HY). When HA is extracted from an animal tissue, usually, a large amount of proteins go into solution along with it. The amount of protein can vary substantially depending upon the nature of the tissue and the parameters of the extraction. In extraction of HA from rooster combs, the weight ratio of HA to proteins can vary from 1:0.5 up to 1:4 (U.S. Pat. No. 4,303,676, E. A. Balazs). As a result, the first problem in recovery of pure HA from animal tissue is the removal of proteins. We have found that the above mentioned preliminary treatment of the tissue provides a water extract of HY with a substantially lower protein content than in the absence of such treatment.

The precise nature of the chemical events occurring during the treatment of the tissue is not fully understood and, therefore, the invention should not be limited by any specific chemical reaction. It is believed that, as a result of chemical reactions between proteins in the tissue and a reagent in the treating mixture, the proteins become denatured and immobilized in the tissues and are therefore insoluble in the subsequent aqueous extraction.

Any substance which reacts with proteins in a water-containing medium can be used for the purpose of the present invention. We have found that the most advantageous substance is formaldehyde. Other aldehydes such as glutaraldehyde or glyoxal also can be used in the method according to the present invention.

The treatment of the tissue can be carried out in a water solution of the reagent. However, if this is done, there will be a substantial loss of HY because of its good solubility in water. For this reason, it is preferable to carry out the treatment of the tissue in a mixture of water and a water-miscible organic solvent. The solvent should not react with the reagent used for the protein immobilization. Among these solvents are lower ketones such as acetone or methyl ethyl ketone, alcohols such as ethanol or isopropanol, aprotic solvents such as dimethylformamide, dimethylacetamide or dimethylsulfoxide and others. When such a solvent is mixed with a tissue which contains a large amount of water, usually 80-90% or more by weight, a water-solvent mixture is formed. The water-solvent ratio in the mixture can be adjusted to any desired level by changing the solvent/tissue ratio or by adding water to the mixture. The preferable water/solvent ratio is determined by HY solubility in the sense that the HY should not be soluble in the mixture used for the treatment of the tissue. The HY solubility depends upon the type of solvent used, water/solvent ratio, the presence and concentration of any electrolyte in the mixture and the pH of the mixture. The HY solubility can be substantially reduced by introducing an electrolyte into the mixture. Any type of electrolyte can be used which is soluble in the water-solvent mixture and which provides the desired pH of the mixture. For example, when acetone is used as a solvent sodium acetate can be conveniently used as a soluble electrolyte.

The composition of the mixture for treating the tissue can vary over a broad range depending upon the nature of the tissue, the type of solvent used, the type of electrolyte, etc. As mentioned above, HY from the tissue should not be soluble in the treating mixture but the latter should contain enough water to allow the tissue to swell so as to facilitate the reaction between the reagent and the tissue polymers. We have found that in the case of rooster combs as a source of HY, the composition of the mixture, taking into account the water from the combs, can be in the following range, % by weight: water 10-50, solvent 40-85, electrolyte 0-20, reagent 0.2-10. Several different solvents can be used in the same treating mixture, if desired. We have found it to be advantageous to use small amounts of water-immicsible solvents, such as chloroform, in the treating mixture. The content of these solvents in the mixture can be from 0.5 to 10% by weight.

The pH of the treating mixture can be varied depending upon the nature of the reagents, composition of the mixture, temperature and time of the treatment. In recovery of HY from animal tissues according to the present invention, the following considerations are very important. Some of the reagents, formaldehyde, for example, can react with hydroxyl groups of HA macromolecules at low pH to give a cross-linked polymer, insoluble in water. A prolonged treatment in a medium with a relatively high pH leads to the degradation of HA and only a low molecular weight polymer can be recovered. We have found that when an aldehyde type of reagent is used according to the present invention the best results are obtained with pH close to neutral, for example, in the range from 4 to 10.

The ratio of the treating mixture to the tissue can vary over broad limits. The lower limit is determined, usually, by the provision that the tissue, which is quite bulky in the case of rooster combs, should at least be fully covered with the mixture. The upper limit can be chosen based on economical consideration. In treatment of rooster combs according to the present invention, the ratio of the treating mixture to the tissue (calculated on dry weight of the tissue) is usually more than 10:1.

The temperature affects the efficiency of the treatment according to the present invention. However, since HY is susceptible to hydrolysis at elevated temperature, it is preferable to carry out the treatment at room temperature or below in order to obtain a high molecular weight product.

The time needed to perform the treatment depends upon many factors including the composition of the mixture, the nature of the tissue, temperature, etc. It is assumed that the limiting factor in the treatment is the diffusion of the reagent into the tissue slices. For this reason, the size of these slices is an important parameter. We have found that in treatment of rooster combs sliced into pieces of 1-3 mm thickness, the time of the treatment can be in the range of 4-24 hours.

The tissue treated as described above is then washed with a solvent or a solvent/water mixture to remove the excess treating mixture from the tissue. It is convenient to use the same solvent as is used in the mixture for the tissue treatment. One can use any number of washings but, it has been found that one washing gives satisfactory results.

The washed tissue is then directly extracted with water to recover the HY. We have found that the efficiency of the extraction depends upon the water/tissue ratio, pH of the extracting media, temperature and time. We have also found that the efficiency of the extraction of the treated tissue can be substantially increased by first drying the treated tissue to remove the solvent which was used in the treating and washing steps. The best results are obtained when the tissue is dried to ¼ to ½ of its original weight.

The water/tissue ratio in the extraction step is chosen based on several considerations. First of all, there should be enough of the liquid phase to cover the tissue during extraction. On the other hand, the amount of water should not be too large in order to have as high a concentration of HY in the extract as possible so as to reduce the amount of precipitant in the next step of the process. We have found that in the case of rooster combs the preferred ratio of water tissue is from 2 to 5 based on the weight of the untreated combs.

The pH of the extracting media can be kept neutral, acidic or alkaline depending upon the desired quality of the end product. We have found that in order to obtain ultra high molecular weight product, the pH of the extracting media should be in the range of 6-8.5. A higher pH leads to an increase in the HY concentration in the extract but, at the same time, to a decrease in the molecular weight of the product and to changes in other polymer properties which will be discussed below in more detail. In any case, by controlling the pH during the extraction step, one can conveniently regulate the properties of the end product in a desired direction.

It is preferable to extract the treated tissue at a temperature less than 25° C. because the degradation of HY at higher temperatures can substantially decrease the molecular weight of the polymer.

The time needed for extracting the maximum amount of HY from the treated tissue varies substantially with other parameters of the extraction, such as pH, liquid/tissue ratio and intensity of stirring. We have found that in the extraction of rooster combs with water, good results can be obtained when the treated combs are extracted for from 6 hours to several days.

The mixture of treated tissue and extracting media can be stirred during the extraction or left without any stirring. Clearly, stirring will increase the diffusion rate of HY molecules from the tissue into the extract. On the other hand, vigorous stirring can lead to degradation of HY and, hence, to a decrease in the molecular weight. In addition, we have found that vigorous stirring causes tissue disintegration which makes it difficult to separate the tissue from the extract. Therefore, it is preferable to carry out the extraction step without or with very slow and gentle stirring.

After extraction, the tissue is separated from the extract using any of several conventional methods including filtration, centrifugation, decantation and the like. We have found that the most simple and economical way is filtration. Depending upon the kind of tissue used as a starting meterial, it may be preferable to use a two-step filtration. Thus, in the case of rooster combs, large pieces of tissue can be easily separated by filtration through a nylon mesh and the fine purification of the extract can be achieved by filtration through any dense filter media, e.g., a cellulosic material.

The HY concentration in the extract depends upon many factors including pH during extraction, time, liquid/tissue ratio, and intensity of stirring. Usually it is in the range of from 0.3 to 3.0 mg/ml and, sometimes, even higher. In some cases, when the HY concentration in the extract is on the lower side, we have found it desirable to run a second extraction of the tissue. We have also found that the product precipitated from the second extract usually has a higher molecular weight as compared to the HY from the first extract. This can be explained by the fact that low molecular weight fractions of HY diffuse more easily from the tissue into the extract and the product precipitated from the first extract is enriched with these fractions.

One can use more than two extractions to achieve as high a yield as possible, but the concentration of HY in an extract decreases with each consecutive extraction.

HY can be recovered from the filtrates by any method known in the prior art. The most convenient method is precipitation with a water-miscible solvent such as acetone, ethanol, isopropanol, etc. The precipitation can be done in the presence of an acid such as hydrochloric, sulfuric, phosphoric, etc., or in the presence of neutral electrolytes such as sodium acetate, sodium chloride and their salts. HY and its salts are usually precipitated as a white fiber-like material or a powder. The precipitate can be washed with the same solvent which is used for precipitation, or with any other solvent mixture which will not dissolve the product, for example, ether. The washed product can be dried with any conventional means or can be stored under a layer of a solvent such as acetone, ethanol, etc. Alternately, the filtrate can be freeze-dried.

It is clear that any additional steps known in the prior art and used in HA purification can be included in the process according to the present invention without limiting its scope. For example, to remove pyrogens or inflammatory agents, extraction by well known solvents, such as chloroform, in which HY is insoluble but lipoproteins, glycolipids or glycolipoproteins are soluble or separated, can be used.

The process according to the present invention allows one to obtain HY products with properties varying over a broad range. The following properties were evaluated. The cited methods were used to characterize the products obtained according to the present invention.

The HY concentration in solutions was determined by hexuronic acid assay using the automated carbazole method (E. A. Balazs, K. O. Berntsen, J. Karossa and D. A. Swann, Analyt. Biochem. 12, 547–558 (1965)). The hexosamine content was determined by the automated colorimetric method (D. A. Swan and E. A. Balazs, Biochem. Biophys. Acta 130, 112–129 (1966)). Protein content of HY solutions was determined by the phenol reagent method (Lowry et al., J. Biol. Chem 193, 265–275 (1951)).

The formaldehyde content in the product was determined by hydrolysis of about 0.1 g of the sample in 10 ml of 10% aqueous sulfuric acid for 2 hours with boiling followed by steam distilling free formaldehyde off the solution obtained and determing formaldehyde in the distillate using a colormetric method with chromotropic acid (M. J. Boyd and M. A. Logan, J. Biol. Chem., 146, 279 (1942)).

The limiting viscosity number (intrinsic viscosity) defined as lim (n/no-1)/c where n and no are the viscosities of the solution and the solvent respectively, and c the concentration of HY in g/cc. The measurements were carried out in aqueous 0.20 M NaCl solutions in an Ubbelohde capillary type dilution viscosimeter. The viscosity-average molecular weight is calculated by the equation $[n] = 0.0228 M^{0.81}$ (R. C. Cleland and J. L. Wang, Biopolymers 9, 799 (1970)).

The weight-average molecular weight is determined by the low angle laser light scattering method using a Chromatix KMX-6 instrument equipped with a helium-neon laser set at 632.8 nm. The weight-average molecular weight is also calculated from the sedimentation and diffusion constants determined in an analytical ultracentrifuge.

The dynamic light scattering method is used to evaluate the aggregation of the molecules in relatively concentrated solutions of HY. This method gives the distribution of equivalent spherical diameters (ESD) in solution.

Rheological properties were evaluated with the Bohlin Rheometer System which is a computerized rheometer.which can operate in three modes: viscometry, oscillation and relaxation. The following parameters are measured for the HY solution: viscosity for the broad range of shear rates, dynamic viscosity, dynamic storage moduli and dynamic loss moduli for various oscillation frequencies and relaxation time.

As mentioned above, the product according to the present invention (HY) is a new polymer, obtained as a result of an in situ chemical reaction between HA and a cross-linking agent, such as formaldehyde. We have found, by chemical analysis of HY, that the content of the combined formaldehyde in products obtained from the rooster combs treated with a formaldehyde-containing mixture, was in the range of from 0.005 to 0.02 wt. % calculated on the weight of polymer, depending upon the various parameters of the treatment.

The presence of the combined formaldehyde in the product was also proved by an experiment in which the treatment was carried out with radiolabeled formaldehyde $^{14}CH_2O$ (see example 12 below). The results of the experiment show that the product obtained according to the invention contained combined formaldehyde which could not be removed by repeated precipitations or by exhaustive dialysis of the polymer solutions This is strong evidence for the evidence of covalent bonding of formaldehyde to the polymeric molecules of the product. In order to find out whether formaldehyde is specifically combined with HA, the latter was treated with bacterial or leech hyaluronidases, enzymes specifically degrading HA. The results of this treatment showed that a noticable amount of formaldehyde was covalently attached directly to the HY macromolecules.

The protein content in the product obtained according to the present invention is usually not more than 0.5% as calculated on the weight of a dry polymer and can be as little as 0.1% and even less.

The chemical modification of hyaluronic acid by covalent attachment of a cross-linking agent to its macromolecules, in other words the changes in the primary structure of the polymer, substantially affect its physicochemical parameters such as molecular weight and molecular size, intermolecular interaction, and rheological properties of polymer solutions, as well.

HY obtained according to the present invention can have a very high molecular weight. Thus, the limiting viscosity number can be higher than 7,000 cc/g which corresponds to a viscosity-average molecular weight of around $6 \times 10^6$. The weight-average molecular weight from the light-scattering data can reach a value of $13 \times 10^6$. We have found that this discrepancy between the weight-average and the viscosity-average molecular weights to be quite meaningful as is discussed below. It should be understood that a polymer with substantially lower molecular weight, e.g., $1 \times 10^6$ or less, can be easily obtained with the method according to the present invention, if desired. Similarly, a polymer with any desired molecular weight can be obtained if HY, at any stage of its recovery and purification, is exposed to agents which are known to break the glucosidic bond of the polysaccharide chain. Such well known agents are specific enzymes, .e.g, hyaluronidase, free radical generating systems, shear forces, heat, strong alkalies and acids, etc.

The partial specific volume (psv) of HY in solution depends upon the ionic strength of the solution. It was determined by densitometry for HY solution in water containing 0.15 M of NaCl in the concentration range from zero to 0.5 mg/ml and was found to be 0.627 cc/g.

Figure 4:
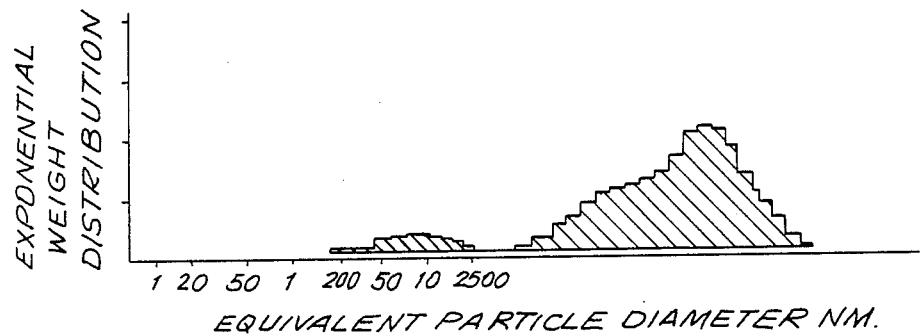
FIG. 4 is a graph showing the distribution of ESD for a 1% (wt.) solution of HY (limiting viscosity number 4,300 cc/g.) in aqueous 0.15 M NaCl.

The distribution of ESD for a sample of HY dissolved in 0.15 M NaCl solution in 1% solution is presented in FIG. 4. It is apparent from the data presented that HY exists in a very highly aggregated form, although these aggregates are stable and do not sediment.

Figure 2:
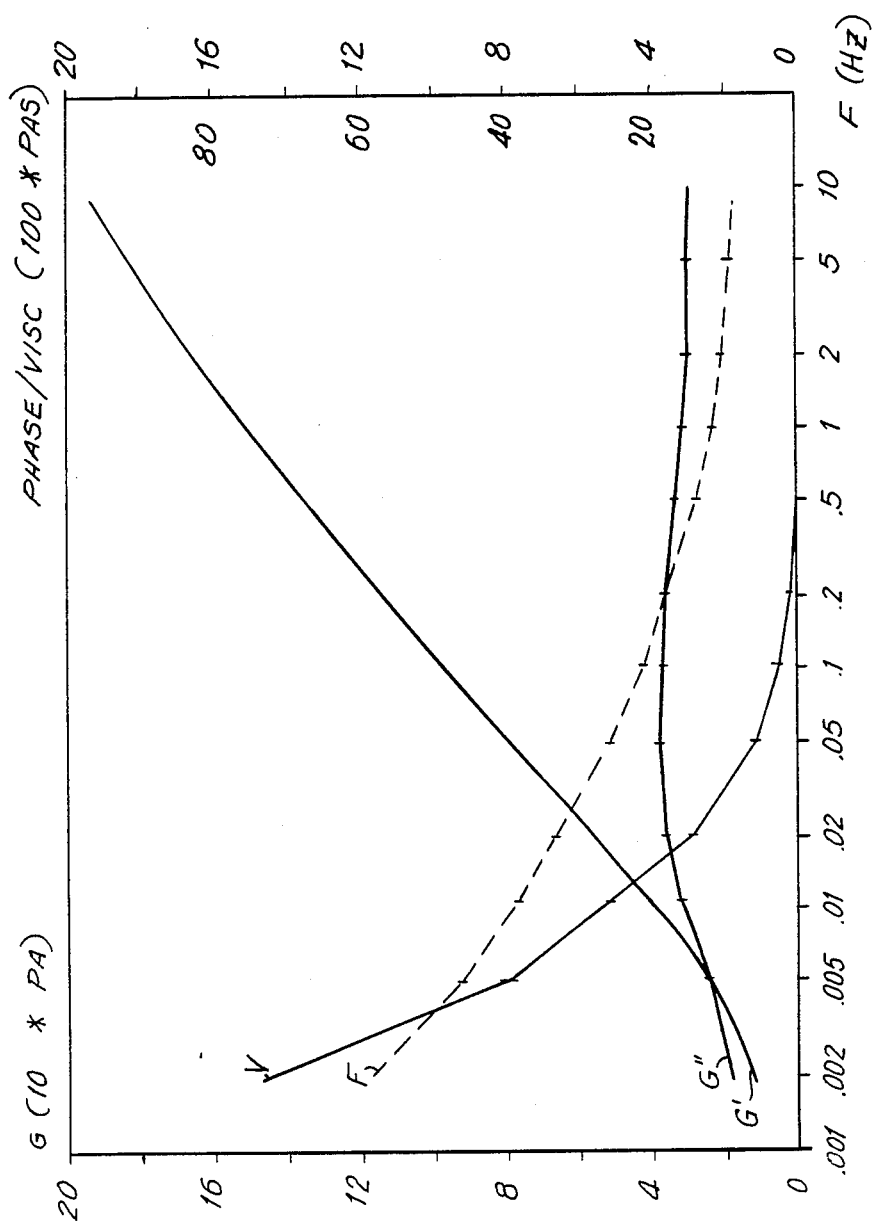
FIG. 2 is a graph giving the results of an oscillation test for a 1% (wt.) solution of HY in aqueous 0.15 M NaCl (V=viscosity; F=phase angle; G'=dynamic storage moduli; G"=loss moduli)
Figure 3:
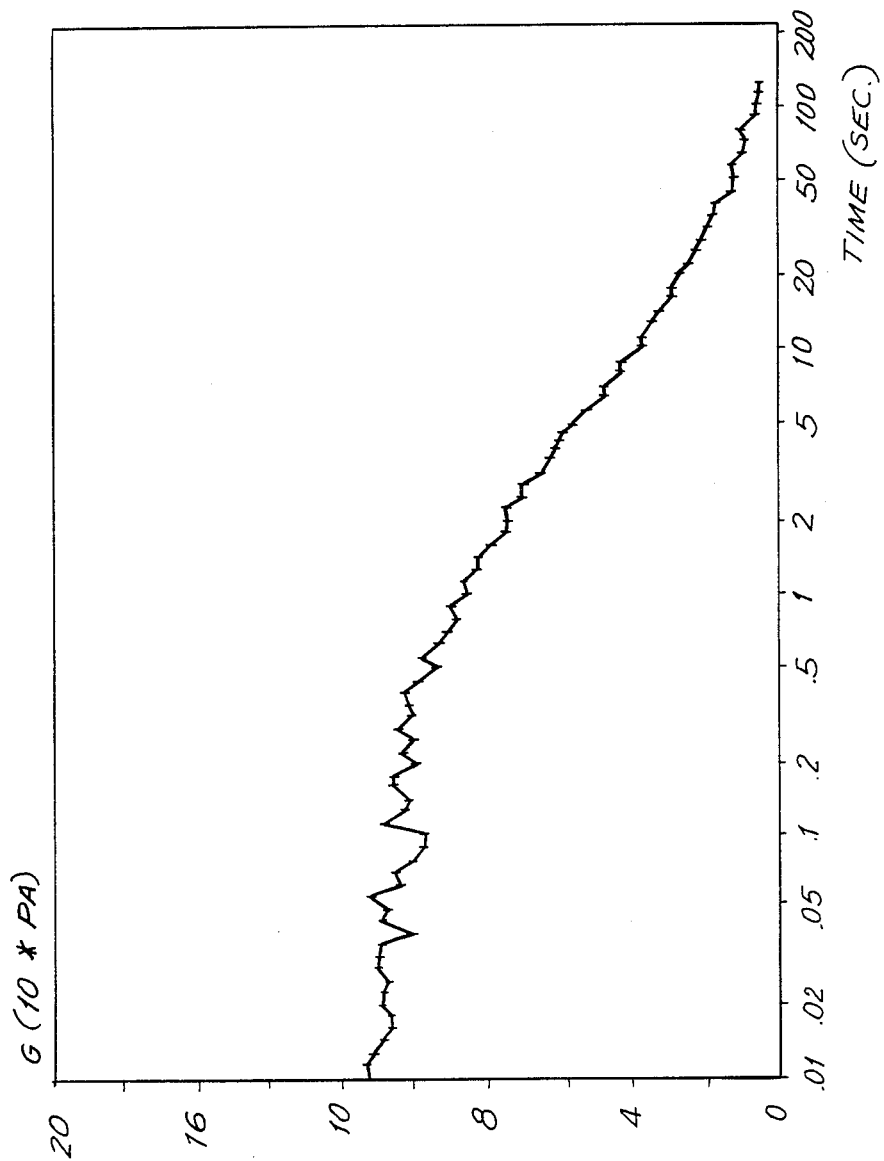
FIG. 3 is a graph showing the relaxation curve for a 1% (wt.) solution of HY in aqueous 0.15 M NaCl.

The rheological properties of a typical ultra-high molecular weight product prepared according to the present invention are presented in FIGS. 1-3. We have found that this product forms solutions (0.5 wt % and higher) with remarkable viscoelastic properties.

The following parameters characterize the elastic properties of the polymer solutions in the best way: dynamic storage moduli ($G'$), the frequency of "cross-over point" (a point at which dynamic storage module $G'$ becomes greater than dynamic loss moduli $G''$), phase angle and relaxation time.

HY forms very viscous solutions in water or water solution of electrolytes. The viscosity of the solution depends upon the polymer concentration, electrolyte content, temperature and decreases with shear rate, i.e., the HY solutions have substantial pseudoplasticity.

When the rheological properties of HY solutions are considered, one should understand that these properties are greatly dependent upon the molecular weight of the product, as in the case of any other polymer. It was mentioned above that HY can be obtained with a molecular weight varying over a broad range and the rheological properties will vary accordingly. Thus, we have found that for the ultra-high molecular weight product (limiting viscosity number higher than 4500 cc/g) the viscosity of 1 wt % solution in 0.15 M NaCl solution in water is up to 1000 Pa.s and even higher at shear rate 0.055, whereas it is only about 2 Pa.s for 1 wt % solution of polymer with limiting viscosity number about 1000 cc/g. We have found that the elastic properties of HY solutions also depend upon the polymer molecular weight. Thus, the dynamic storage module $G'$ for a 1 wt % solution of ultra-high molecular weight HY in 0.15 M NaCl is about 40 Pa at a frequency 0.01 Hz, whereas it is only about 0.2 Pa for a solution of HY with limiting viscosity number about 1000 cc/g. The frequency of the "cross-over point" which characterizes in a very good way the ratio between elastic and viscous properties of polymer solutions is usually less than 0.025 Hz for 1 wt % HY solutions in 0.15 M NaCl at 25° C. when molecular weight of the polymer is in the range from about $1.5 \times 10^6$ to $8 \times 10^6$ and higher.

Figure 5:
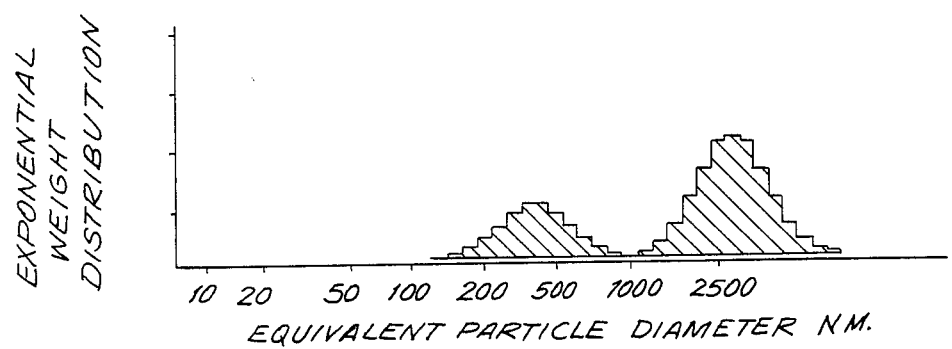
FIG. 5 is a graph showing the distribution of ESD for a 1% (wt.) solution of HA (limiting viscosity number 3,562 cc/g.) in aqueous 0.15 M NaCl.

The physicochemical and rheological properties of an HY sample and its solution were compared with the same properties of an HA product obtained according to a well known method and are presented in Table 1 and in FIGS. 4 and 5. The product used for comparison is HA recovered from rooster combs by water extraction followed by deproteinization with the so-called Sevag procedure, which entails several chloroform extractions (G. Blix, O. Shellman, Arkiv for Kemi, Mineral Geol. 19A, 1 (1945)).

TABLE 1
COMPARATIVE PHYSICO-CHEMICAL AND RHEOLOGICAL DATA FOR HY AND HA SAMPLES

| Parameter | HY | HA |
| --- | --- | --- |
| Limiting viscosity number, cc/g | 4,729 | 3,562 |
| Molecular weight from viscosimetry data, $\times 10^6$ | 3.28 | 2.30 |
| Molecular weight from light-scattering data, $\times 10^6$ | 13.30 | 2.86 |
| Molecular weight from sedimentation, diffusion data, $\times 10^6$ (PSU) | 13.60 | 2.14 |
| Partial specific volume, cc/g | 0.627 | 0.570 |
| Rheological properties of 1 wt % solution in 0.15 M aqueous NaCl: Shear viscosity at shear rate $0.055^{-1}$, Pa.s | 969 | 305 |
| Dynamic storage moduli (G') at frequency 0.01 Hz, Pa | 39.8 | 10.1 |
| Frequency at "cross-over point", Hz | 0.0056 | 0.035 |
| Relaxation time to reduce moduli by half | 58 | 19 |
| Phase angle, degrees | | |
| at frequency 0.002 Hz | 58.7 | 76 |
| at frequency 10 Hz | 8.5 | 12 |

The data presented in Table 1 and in FIG. 4 show distinctive differences between HY and HA. First, the viscosity-average molecular weight and weight-average molecular weight for the known product have approximately the same values (the weight-average molecular weight is slightly lower), whereas for the product according to the invention the weight-average molecular weight is about four times higher than the viscosity-average molecular weight. Second, the greater value for psv of HY solution as compared to HA proves that HY macromolecules have a larger size. Third, the aggregation of HY macromolecules in solution provides substantially larger aggregates as compared to HA solutions which suggest not only larger size of HY macromolecules but also much stronger intermolecular interaction. Finally, HY solutions are substantially more viscous and elastic than equiconcentrated solutions of HA. Though the increased viscosity can be attributed to a higher viscosity-average molecular weight, the observed dramatic increase in elasticity hardly can be explained by the same reason.

All these observations lead us to a conclusion that the chemical modification of hyaluronic acid in situ prior to its extraction from the tissue, though resulting in only minor changes in the chemical composition of the polymer provides, at the same time, some dramatic changes in the physicochemical parameters and rheological properties. This can only occur when the change in chemical composition corresponds to some major changes in the macromolecular structure.

The shape and conformation of HA macromolecules in solution have been studied by various methods and there is a large body of literature on this subject. These studies indicate that the macromolecules have an extended random coil configuration and entangle with each other a relatively small (e.g., 0.1%) concentration of the polymer in the solution. At higher concentration the solution is believed to contain a continuous three-dimensional network of polymeric chains. The glucosidic linkages in the HA macromolecules have been found to possess a considerable stiffness. Several mechanisms, such as solvent-solute interaction, interaction with small amounts of proteins present in many HA preparations, and inter-chain interactions were proposed to explain these phenomena. (See, e.g., E. A. Balazs, Physical Chemistry of Hyaluronic Acid, Fed. Proceed., 17, 1086–1093 (1958).) Some authors have proposed a double helical structure for HA macromolecules and suggested that double helical segments could play the role of cross-links providing the unusual rheological properties of HA solutions (C. M. Dea, R. Moorhous, D. D. Rees, S. Arhott, J. M. Guss and E. A. Balazs, Science, 179, 560–562 (1972); S. Arnott, A. R. Mitra and S. Raghunatan, J. Mol. Biol. 169, 861–872 (1983)).

Taking into consideration these studies and observations, we have come to a hypothesis that the product according to the present invention (HY) can contain an additional number of cross-links introduced during the treatment of the tissue with a protein cross-linking immobilizing agent. The agents used according to the present invention, such as formaldehyde, are very reactive towards various chemical groups, their reactivity depending substantially on such reaction conditions as pH, temperature, concentration, etc. The hydroxyl groups of hyaluronic acid evidently do not react with these agents under the treatment conditions since the product obtained after treatment is always soluble in water and, hence, does not have substantial degree of cross-linked polymer. The amount of additional cross-links introduced into the polymer during the treatment is probably small enough not to cause the insolubility of polymer, but significant enough to markedly increase interaction between macromolecules and consequently the elasticity of the polymer solution. Several candidates for such reaction with a treating agent are the acetamido groups of hyaluronic acid, nonacetylated amino groups which can be present in small amounts in hyaluronic acid, and amido, amino and other reactive groups of proteins which are present in the intercellular matrix of the tissue during the treatment. It is hardly probable that the acetamido groups of HA themselves can provide intermolecular cross-linking. In the studies of the reaction of proteins with formaldehyde (see, e.g., J. F. Walker, Formaldehyde, Reinhold Publ. Corp., NY, 1953, pp 312–317), it was found that amide groups of a protein themselves could not provide cross-linking and one of the most probable reactions in the cross-link formation is a reaction of formaldehyde with amino groups giving N-methylol amino groups which, in turn, react with amide groups.

Accordingly, two mechanisms are possible for introducing a limited number of cross-links into HA macromolecules. The first mechanism involves the reaction between a cross-linking agent, such as formaldehyde, and acetamido and free amino groups of HA, the existence of which in HA is quite probable (E. A. Balazs, Fed. Proceed. 25, 1817–1822 (1966)).

The second possible mechanism suggests the participation of proteins or polypeptides in the cross-linking reaction. Reports persist in the literature that proteins or polypeptides are covalently linked to the HA molecule (Yuko Mikum-Takagaki and B. P. Toole, J. Biol. Chem. 256 (16), 8463–8469 (1981)) or can be associated with HA molecules in another way. In this case, cross-links can be formed between one HA macromolecule and a protein moiety and another HA macromolecule, or between a protein covalently attached to two HA macromolecules.

None of these mechanisms should be considered as limiting the present invention. It should be understood that other mechanisms for introduction of small amounts of covalent cross-links into the product according to the present invention are possible.

In any case, the essential feature of the present invention is the chemical modification of HA in the tissue during the process of its recovery, presumably by introducing small numbers of cross-links in the HA macromolecules, the degree of modification being enough to substantially increase the elastic characteristics of the polymer solutions without any adverse effect on the beneficial properties of HA, such as its ability to give highly viscous solutions in aqueous medium, biocompatibility, etc.

The chemically modified hyaluronic acid, HY, prepared according to the present invention can be successfully used for many applications in the biomedical field and in cosmetics, for example, as a tool in viscosurgery, for coatings to improve the biocompatibility of various materials, as a component of various pharmaceutical preparations, in skin care products, etc. The improved properties of this polymer, such as an increased elasticity, give substantial benefits when HY is used.

Figure 6:
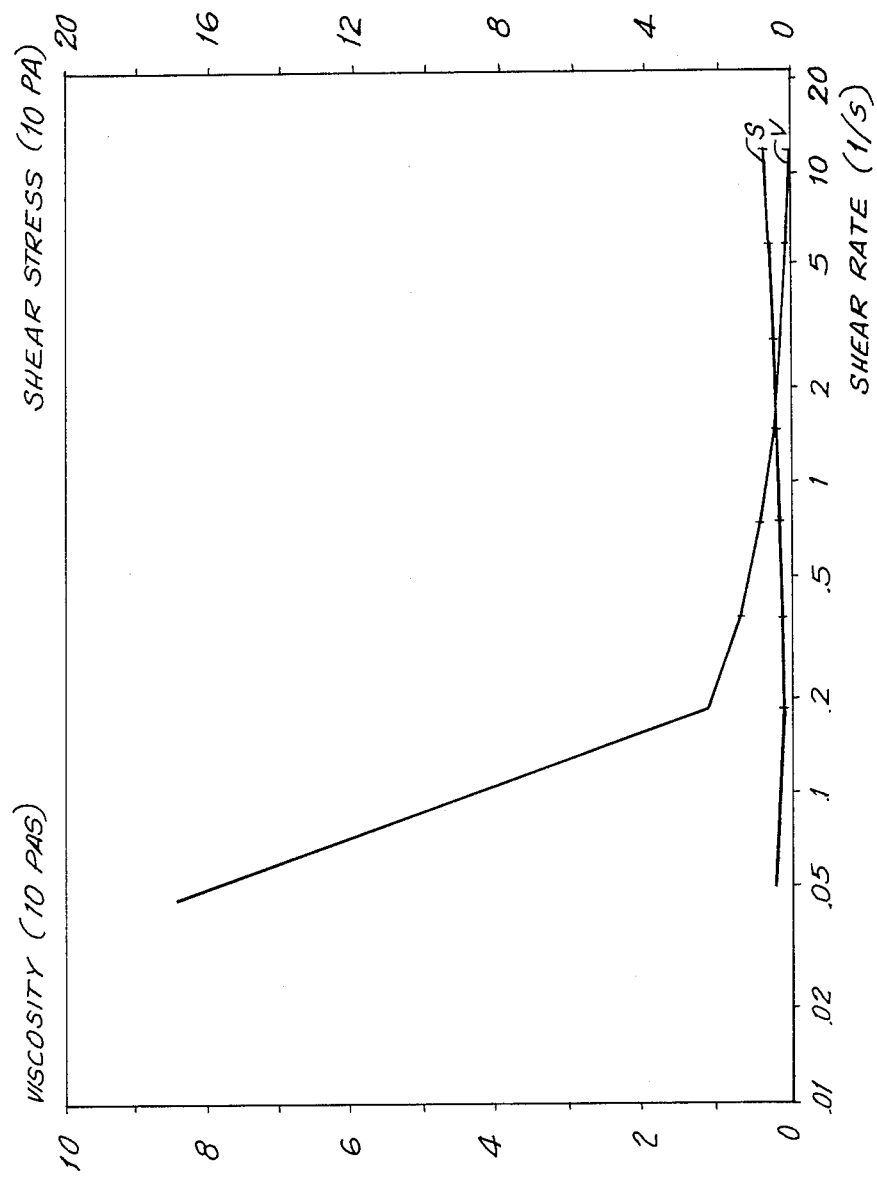
FIG. 6 is a graph showing viscosity vs. shear rate dependence for a jelly-type product according to the invention.
Figure 7:
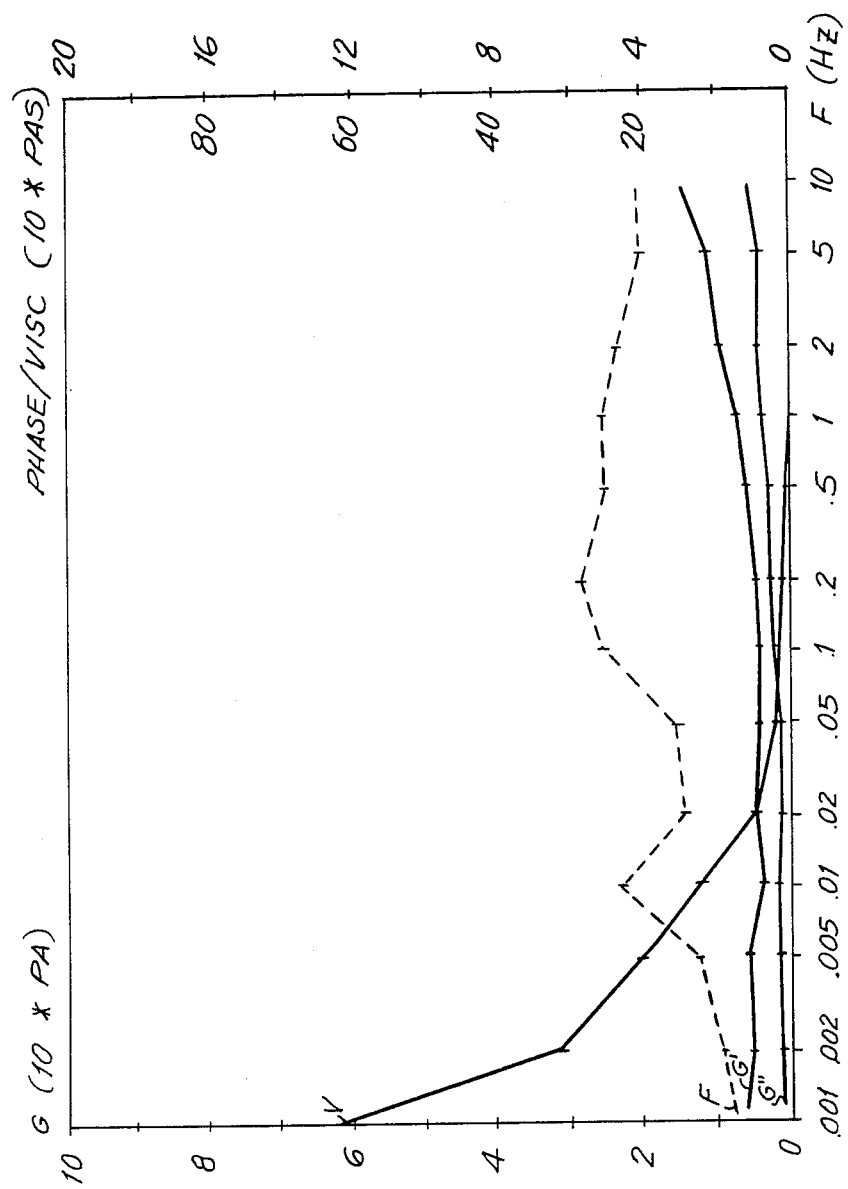
FIG. 7 is a graph showing the results of an oscillation test for a jelly-type product according to the invention (V=viscosity; F=phase angle, G'=dynamic storage moduli; G"=loss moduli)
Figure 8:
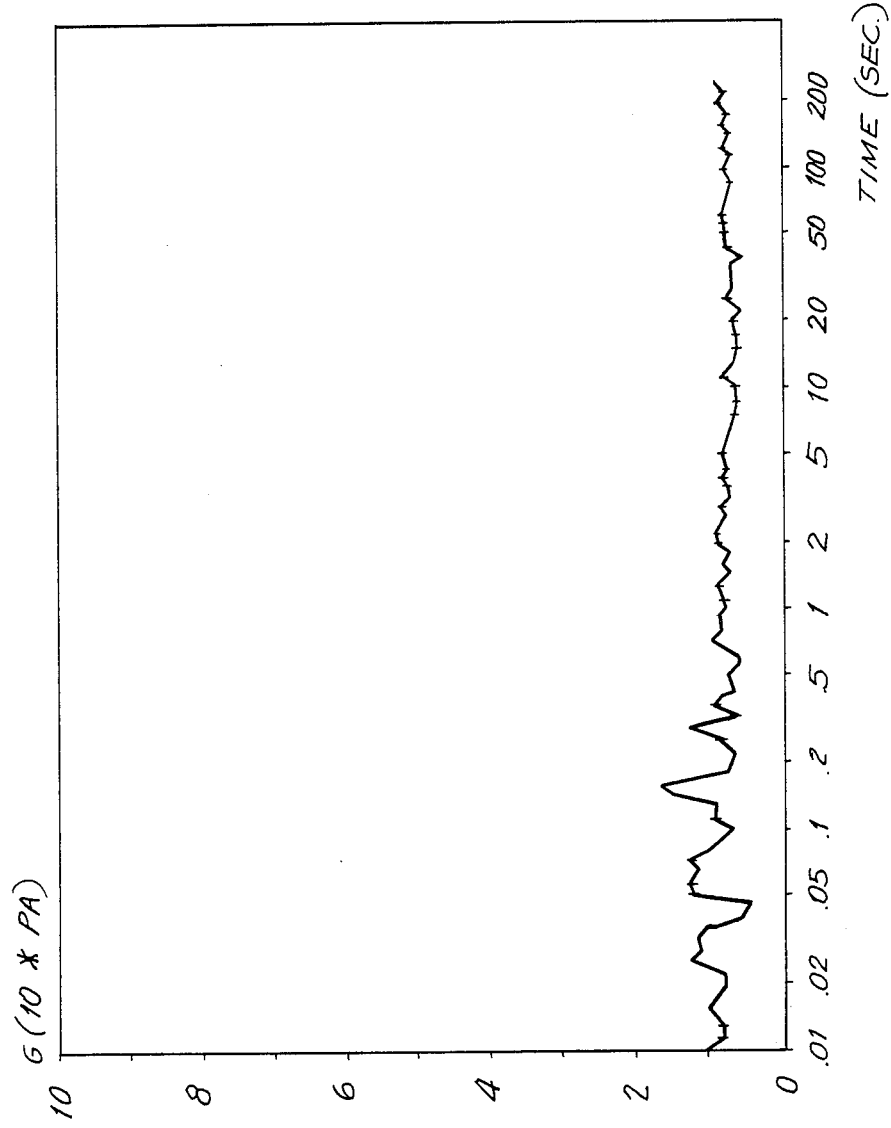
FIG. 8 is a graph showing the relaxation curve for a jelly-type product according to the invention.

HY can also be used as a starting material for new products obtained through additional chemical modification, such as cross-linking with conventional cross-linking agents. We have found that the special properties of chemically modified HA according to the present invention and its solutions provide an opportunity to obtain the above mentioned additionally modified products which also possess some unusual properties. Thus, we have found that a water-insoluble jelly-like material can be obtained from the product according to the invention by cross-linking with divinyl sulfone in alkaline solution. This material is a highly swollen gel. The concentration of the polymer in the gel depends upon the composition of the liquid phase which can be water or water solutions of various low-molecular weight substances, such as electrolytes. In the case of physiological salt solution (0.15 M NaCl in water), the polymer concentration can be in the range from 0.15 to 0.40 wt %. This material possesses very interesting rheological properties (FIGS. 5, 6 and 7). Thus, the elastic component of the complex dynamic moduli (G') is higher than the loss moduli (G") for all tested frequencies. At the same time, the material behaves like a pseudo-plastic body at low shear rates, i.e., it has a substantial viscosity which decreases with shear rate. This material is also characterized by a very long relaxation time. We strongly believe that this is a unique structure of solutions of HY obtained according to the present invention which makes it possible to obtain the above described jelly-type product with these special rheological properties. In other words, the chemical changes in HA occurring in the recovery process according to the present invention affect not only the structure and properties of HY but also the properties of products obtained therefrom. Accordingly, we have found that when HA obtained according to methods known in the art, namely, by protein removal with chloroform extrations, was used as a starting material for cross-linking with divinyl sulfone, an insoluble material was obtained with rheological properties substantially worse than those of the present invention.

It should be understood that many other modified materials can be obtained through additional modification of the product obtained according to the present invention, such as strongly cross-linked gels, insoluble films, coatings, etc.

The following examples illustrate preferred embodiments of the invention, without however, being a limitation thereof.

EXAMPLE 1

Rooster combs were extensively washed with a 1% water solution of cetylpyridinium chloride, then with deionized water and, finally, were frozen. The frozen combs were cut with a slicer to pieces about 1-2 mm in thickness. A mixture containing 1000 g of acetone, 100 g of 37% formalin and 50 g of sodium acetate was prepared and 1000 g of sliced combs were added to it. The mixture of combs and the treating liquid (pH 6.7) was kept for 24 hours at a temperature of about 20° C. with slow stirring. The liquid was then separated from the combs by filtration through a nylon screen. The treated combs were then washed with 500 g of acetone and dried in air to a final weight of 500 g. The dried combs were mixed with 2.5 l of deionized water and the extraction was carried out for 72 hours at a temperature of about 20° C. with slow stirring. The combs were separated from the extract by filtration through a nylon mesh fabric and the extract was additionally filtered through cellulosic type filter material ("Micromedia" ®, M70, Ertel Engineering Co.). The HA concentration in this first extract was 0.92 mg/ml. 2 l of the extract was mixed with 4 l of acetone and 20 g of sodium acetate. A white fibrous precipitate formed which was collected, washed with acetone and dried in a vacuum-oven at 35° C. 1.75 g of product were obtained. Hexosamine/hexuronic acid ratio for the product was found to be 1±0.05. The formaldehyde content in the product was found to be 0.0150%. Thus, the product was identified as Hylan. The protein content in the product was 0.35% and the limiting viscosity number was 4,320 cc/g.

The combs after the first extraction were mixed with 2.5 l of deionized water and the extraction was carried out for 48 hours at an ambient temperature. The combs were separated and the extract was filtered as described above. The HA concentration in the second extract was 0.65 mg/ml. 1.26 g of the product was recovered from the extract by precipitation as described above. This fraction was also characterized as chemically modified sodium hyaluronate with the formaldehyde content being 0.014%. The protein content was 0.27% and limiting viscosity number was 4,729 cc/g. Rheological properties of 1 wt % solution in aqueous 0.15 M NaCl solution in water were evaluated. These data are given in Table 1.

A third water extraction of the combs was also performed as described above. The HA concentration in the third extract was 0.33 mg/ml and 0.60 g of HA was recovered from this extract, with protein content 0.20%, limiting viscosity number 4,830 cc/g and formaldehyde content 0.0115%.

Thus, a total of 3.61 g of chemically modified sodium hyaluronate was recovered from 1 kg of rooster combs.

EXAMPLE 2

1 kg of sliced rooster combs prepared as in Example 1 were mixed with a mixture of 1 kg of acetone and 150 g of 40 wt % solution of glutaraldehyde in water. The pH of the mixture was 6.9. The mixture was kept for 16 hours at ambient temperature (about 20° C.) with slow stirring (about 1 rpm). Then the combs were separated from the liquid, washed with acetone and dried in air to one-half of the original weight. The dried combs were extracted with 3 l of deionized water for 96 hours at a temperature about 20° C. The extract was separated from the combs and filtered as described in Example 1.

The HA content in the extract was 1.4 mg/ml. The product, after precipitation with acetone according to Example 1, had protein content of 0.42% and limiting viscosity number 3,700 cc/g.

EXAMPLE 3

The procedure described in Example 2 was repeated with the exception that the same amout of 40 wt % solution of glyoxal in water was used instead of glutaraldehyde solution. The HA concentration in the extract was 0.92 mg/ml. The protein content in the product 0.5% and limiting viscosity number was 3,930 cc/g.

EXAMPLE 4

Rooster combs were washed, frozen, sliced and treated with the acetone-formaldehyde mixture according to Example 1. The combs, after being dried to one-half of the original weight, were extracted with 2.5 l of 0.05 M sodium hydroxide solution in water (pH greater than 11) for 120 hours at a temperature of about 20° C. The extract was separated and filtered as described in Example 1. The HA concentration in the extract was 3.6 mg/ml. A white product was precipitated with acetone-sodium acetate mixture, washed with acetone and dried. 7.5 g of a product with protein content 0.2% and limiting viscosity number 1,310 cc/g was recovered.

EXAMPLE 5

Rooster combs were washed, frozen, sliced and 1 kg of combs were mixed with a mixture containing 1 kg of isopropanol, 100 g of 37% formalin, 50 g of sodium acetate and 100 g of chloroform. The treatment was carried out with slow stirring for 16 hours at a temperature about 20° C. The extraction and precipitation were carried out as described in Example 1. The HA concentration in the extract was 0.68 mg/ml. Protein content in the product was 0.46% and limiting viscosity number was 4,900 cc/g.

EXAMPLE 6

Rooster combs were washed, frozen, sliced, treated with acetone-formaldehyde mixture, washed with acetone, dried and extracted with water as described in Example 1. The extract was mixed with a mixture of 2 l of acetone and 1 l of chloroform. 1.9 g of white fiber-like product with protein content 0.05% and limiting viscosity number 4,400 cc/g was obtained.

EXAMPLE 7

1 kg of sliced combs prepared as described in Example 1 were treated with a mixture containing 1 kg of acetone, 50 g of 37% formalin, and 50 g of sodium acetate for 24 hours at a temperature about 20° C. with slow stirring. The extract was separated and filtered, and the product was precipitated as described in Example 1. 1.6 g of white product with protein content 0.45%, limiting viscosity number 5,300 cc/g and combined formaldehyde content of 0.008% was obtained.

EXAMPLE 8

The procedure described in Example 1 was repeated with the exception that after the acetone-formaldehyde treatment the combs were dried to one-third of their original weight, and the first extraction with water was carried out for 96 hours.

The HA concentration in the first extract was 1.05 mg/ml. The product precipitated from this extract had a protein content 0.25% and limiting viscosity number 4,930 cc/g. Oscillation test of a 1 wt % solution of this product in aqueous 0.15 M NaCl solution gave a "cross-over point" at a frequency of 0.020 Hz.

The HA concentration in the second extract was 0.58 mg/ml. The fraction obtained from this extract had a protein content of 0.19% and limiting viscosity number 7,300 cc/g. The combined formaldehyde content was 0.01%. The frequency of the "cross-over point" in the oscillation test was 0.005 Hz.

In total, 3.5 g of chemically modified HA were recovered with the three consecutive extractions.

EXAMPLE 9

Rooster combs were washed, frozen, sliced and 1 kg of the slices were mixed with 1 kg of acetone, 200 g of 37% formalin and 100 g of chloroform. The pH of the mixture was adjusted to 4.0 with hydrochloric acid. The HA concentration in the first extract was 0.58 mg/ml. The product was recovered from the extract by precipitation with acetone-sodium acetate according to Example 1. The protein content in the product was 0.12%, the limiting viscosity number was 4,025 cc/g. The combined formaldehyde content in the product was 0.02%. The frequency of the "cross-over point" in the oscillation test for a 1 wt % solution of the product in aqueous 0.15 M NaCl solution was 0.006 Hz.

EXAMPLE 10

Rooster combs were washed, frozen, sliced and 1 kg of the slices were treated with acetone-formaldehyde mixture as described in Example 1 with the exception that the pH of the mixture was adjusted to 11.0 with sodium hydroxide. The combs were dried and extracted with water according to Example 1. The HA concentration in the extract was 0.69 mg/ml. The product was precipitated from the extract according to Example 1 with the exception that isopropanol was used instead of acetone. 1.3 g of white fibrous material was obtained which had a protein content 0.45%, limiting viscosity number 5,050 cc/g and a formaldehyde content 0.012%. The frequency of the "cross-over point" in the oscillation test for a 1 wt % solution of the product in aqueous 0.15 M NaCl solution was 0.012 Hz.

EXAMPLE 11

This example illustrates obtaining a jelly-type material from hylan. 0.88 g of the product precipitated from the second extract in Example 1 was mixed with 28.3 g of aqueous 0.05 N NaOH solution in water and the mixture was stirred for 60 minutes at room temperature. To the viscous solution which was obtained, a mixture of 0.26 g divinyl sulfone and 1.0 g of aqueous 0.5 N NaOH was added. The resulting mixture was stirred for 10 minutes and then left for 50 minutes at room temperature. An elastic, colorless and clear gel was obtained. The gel was put into 0.5 l of 0.15 M saline solution and left overnight. Then, the excess liquid was removed from the highly swollen gel and 0.5 l of fresh saline solution was added to the gel and the mixture was left on a shaker for 24 hours. The excess liquid was decanted from the swollen insoluble material. A jelly-type clear material was obtained. The HA concentration in the product was determined as 0.275% by weight. The rheological properties of the material are illustrated in FIGS. 5, 6 and 7.

EXAMPLE 12

Treatment of rooster combs with $^{14}CH_2O$

Radiolabeled paraformaldehyde ($^{14}CH_2O$) with a specific activity of 500 m Ci/g (I2CN Radiochemicals) was mixed in an amount corresponding to 5.0 mCi with 1.0 ml of 37 wt % solution of formaldehyde in water to which 0.1 ml of 1 N sodium hydroxide solution in water was added. The mixture was put into a tightly stoppered container and warmed to 60° C. to dissolve the paraformaldehyde. Then the mixture was cooled to 0° C. and neutralized with 0.ml of aqueous 1 N acetic acid. The radioactivity of the solution obtained was measured in 10 ml of Hydrofluor ® liquid scintillation counting medium (National Diagnostic) using a Searle Isocap 300 liquid scintillation counter with computer correction for efficiency based on the external standard method. The formaldehyde concentration was determined by a colormetric method with chromotropic acid. The measured specific activity of the solution obtained was 0.555 mCi/mmole $CH_2O$. The labeled formaldehyde solution was mixed with 7.5 g of acetone, 1 g of chloroform and 0.5 g sodium acetate. 7.5 g of sliced rooster combs were mixed with the solution and the treatment was carried out for 18 hours at a temperature about 20° C. The combs were separated from the liquid, washed several times with acetone and dried in air to one-half of their original weight. 15 ml of double distilled water were added to the combs and the extraction was allowed to proceed for 96 hours at a temperature of about 20° C. The extract was separated from the combs and filtered through several layers of filter paper (Whatman R ® number 1). The same procedure was repeated to obtain a second extract of the combs. HY was precipitated from the extracts as a white fiber-like material by adding to the extracts $CH_3OONa$ in an amount to give a 1 wt % solution and 4 volumes of 95% ethanol. The fiber-like material was separated, washed extensively with acetone, dried and then redissolved in water to give a solution with HY concentration about 1 mg/ml. The HY was reprecipitated from this solution as described above and again thoroughly washed with acetone and dried. The dry material was once again redissolved in distilled water to give a solution containing 0.84 mg/ml of HY. The specific activity of this solution was measured as giving 194 dpm/$\mu$g HA. Exhaustive dialysis of this solution against 0.05 M phosphate buffer, pH 7.5, containing 0.15 M NaCl reduced the radioactivity to 103 dpm/$\mu$g HY. Exhaustive dialysis of this solution against 4 M guanidium hydrochloride reduced the activity to 101 dpm/$\mu$g HY which indicated that formaldehyde remained in the product even after treatment of the solution under protein dissociative conditions. Based on this measured radioactivity of the product and the specific activity of the starting formaldehyde solution, the content of formaldehyde in relation to HY was calculated as about 0.2 wt %. To evaluate how much of the radiolabeled formaldehyde was associated with HY susceptible to enzymatic degradation with streptomyces hyaluronidase, another solution of the product was prepared which contained 0.8 mg/ml of HY and had the activity of 1,250 dpm/10 $\mu$l of solution. To 2 ml of this solution 0.1 ml of citrate-phosphate buffer (pH 5.6) containing 33 TRU of Streptomyces hyaluronidase (Miles Laboratories, Inc., specific activity 2,000 TRU/mg HA, proteolytic activity less than $5 \times 10^{14}$ units per TRU) was added. To another 2 ml portion of the same solution 0.1 ml of the buffer without the enzyme was added. Both portions were dialyzed for 20 hours against 1000 volumes of the citrate-phosphate buffer. The volumes of the two samples after dialysis were the same. The non-enzyme-treated sample had an HY concentration of 0.76 mg/ml and radioactivity was 552 dpm/10 $\mu$l. The HY concentration in the enzyme treated sample was reduced below detectable levels (10 $\mu$g/ml and the radioactivity was 414 dpm/10 $\mu$l of solution. Thus, the hyaluronidase susceptible radioactivity corresponded to 20 dpm/$\mu$g of HY, which corresponded to 0.049 wt % of formaldehyde associated with enzymatically digestible HY. Such labeled samples of the product were further analyzed by gel permeation chromatography on a 1.6×90 cm glass column packed with glyceryl-CPG 3000, pore size 2869±8.3% (Electronucleonics, Inc.). Degassed 0.02 M Borate buffer (pH 7.5) containing 0.15 M NaCl was used for elution. The excluded volume of the column (Vo) was determined with a sample of HY with molecular weight $4 \times 10^6$ and the total column volume (Vt) was determined with sucrose. Elution was carried out at a flow rate of 10 ml/hr at 6° C. 5 ml fractions were collected and analyzed for HY concentration and radioactivity. It was found that radioactivity coelutes with HY in the void volume, and that enzymatic digestion removes both HY and the radioactivity from the void volume fractions. Calculation showed that the specific activity associated with the void volume HY was 14.6 dpm/$\mu$g HY which corresponds to 0.036 wt % of formaldehyde in the polymer. This figure is in a good agreement with the figure obtained in the dialysis experiment.

Variations and modifications can, of course, be made without departing from the spirit and scope of the invention.

Having thus described our invention what we desire to secure by Letters Patent and hereby claim is:

1. A method of obtaining a chemically modified hyaluronic acid preparation comprising:
   (a) treating animal tissue containing hyaluronic acid with an aqueous treating mixture including, an aldehyde to effect chemical modification of the hyaluronic acid contained in the tissue, in situ,
   (b) removing excess treating mixture from the reaction mixture,
   (c) extracting the chemically modified hyaluronic acid from the treated animal tissue with water,
   (d) separating the extract containing the chemically modified hyaluronic acid from the treated animal tissue, and
   (e) recovering the chemically modified hyaluronic acid from the extract.

2. A method according to claim 1 wherein the aldehyde is formaldehyde, glutaraldehyde or glyoxal.

3. A method according to claim 1 wherein the aqueous treating mixture includes a water-miscible solvent which does not react with the aldehyde.

4. A method according to claim 3 wherein the solvent is a lower ketone, a lower alcohol or an aprotic solvent.

5. A method according to claim 4 wherein the solvent is acetone, methyl ethyl ketone, ethanol, isopropanol, dimethyl formamide, dimethyl acetamide or dimethyl sulfoxide.

6. A method according to claim 3 wherein the aqueous treating mixture includes an electrolyte and a water insoluble organic solvent.

7. A method according to claim 6 wherein the electrolyte is sodium acetate and the water insoluble organic solvent is chloroform.

8. A method according to claim 3 wherein the weight ratio of water to water-miscible solvent in the treating mixture is 1-5:4-8.5 and the weight ratio of water to aldehyde is 1-5:0.02-1.

9. A method according to claim 6 wherein the treating mixture comprises, in parts by weight:

| water | 10-50 |
|---|---|
| water-miscible solvent | 40-85 |
| aldehyde | 0.2-10 |
| water insoluble solvent | 0.5-10 |
| electrolyte | 0-20. |

10. A method according to claim 1 wherein the treating mixture has a pH of 4-10, the weight ratio of treating mixture to tissue to be treated is at least 10:1, and treatment is effected for about 4-24 hours at or below about room temperature.

11. A method according to claim 1 wherein the animal tissue is rooster combs and the combs are cut into slices of about 1-3 mm thickness.

12. A method according to claim 1 wherein excess treating mixture is removed from the reaction mixture by washing the treated tissue with a solvent or a solvent/water mixture.

13. A method according to claim 12 wherein the solvent used for washing the treated tissue is the same solvent as is used in the treating mixture.

14. A method according to claim 1 wherein the extraction of the chemically modified hyaluronic acid is effected at a temperature below about 25° C. for about 6 hours to several days, the weight ratio of water to treated tissue being about 2-5:1 based on the weight of the untreated tissue.

15. A method according to claim 14 wherein the treated tissue is dried to about 25-50% of its treated weight before the extraction step.

16. A method according to claim 1 wherein the extract is separated from the animal tissue by filtration, centrifugation or decantation.

17. A method according to claim 16 wherein separation is effected by filtration.

18. A method according to claim 17 wherein the filtration is a two step procedure, a first, or gross filtration through a wide mesh to remove the pieces of animal tissue and a second, or fine filtration through a cellulosic material.

19. A method according to claim 1 wherein the chemically modified hyaluronic acid is recovered from the extract by precipitation with a solvent, followed by washing and drying the resulting precipitated chemically modified hyaluronic acid.

20. A method according to claim 19 wherein the solvent used for the precipitation is acetone, ethanol or isopropanol.

21. A method according to claim 20 wherein a mineral acid or an electrolyte is added during the precipitation step.

22. A method according to claim 21 wherein the mineral acid is HCl, $H_2SO_4$ or $H_3PO_4$ and the electrolyte is sodium acetate or NaCl.

23. A method according to claim 1 wherein the chemically modified hyaluronic acid is removed from the extract by lyophilization.

24. A method of cross-linking the chemically modified hyaluronic acid obtained according to the method of claim 1, which comprises subjecting said chemically modified hyaluronic acid to a cross-linking reaction with divinyl sulfone under alkaline conditions at room temperature for about one hour.

25. A product produced by the method according to claim 1.

26. A product produced by the method according to claim 24.

27. A chemically modified hyaluronic acid preparation characterized by the presence of about 0.005 to 0.05% by weight of aldehyde cross-linking groups covalently bonded to the hyaluronic acid polymer chains.

* * * * *